United States Patent [19]

Wands et al.

[11] Patent Number: 4,870,026

[45] Date of Patent: Sep. 26, 1989

[54] NON-A, NON-B. HEPATITIS, VIRUS, METHODS OF IDENTIFICATION PURIFICATION, CHARACTERIZATION, DIAGNOSIS AND IMMUNIZATION

[75] Inventors: Jack Wands, Waban, Mass.; David Shafritz, Larchmont, N.Y.

[73] Assignees: The General Hospital Corporation; The Albert Einstein College of Medicine of Yeshiva University, both of Boston, Mass.

[21] Appl. No.: 577,324

[22] Filed: Feb. 8, 1984

Related U.S. Application Data

[63] Continuation of Ser. No. 418,708, Sep. 16, 1982, abandoned.

[51] Int. Cl.$^4$ ...................... G01N 33/53; A61K 39/42
[52] U.S. Cl. ........................................ 436/548; 424/89; 424/85.8
[58] Field of Search .................... 424/89, 86; 435/240, 435/7; 436/548

[56] References Cited

U.S. PATENT DOCUMENTS

| | | | |
|---|---|---|---|
| 4,271,145 | 6/1981 | Wands et al. | 424/85 |
| 4,291,020 | 9/1981 | Tabor et al. | 424/89 |
| 4,356,164 | 10/1982 | Tabor et al. | 424/89 |

OTHER PUBLICATIONS

Robinson, "The Enigma of Non-A, Non-B Hepatitis", Journal of Infectious Diseases, vol. 145, No. 3, Mar. 1982.
Wands et al, The Lancet, Saturday, May 1, 1982.
Wands et al, Proceedings of the National Academy of Sciences USA, vol. 79, pp. 1277–1281 (Feb. 1982).
Tabor et al., *Journal of Medicinal Virology* 4:161–169 (1979).
Alter et al., 1981 International Symposium on Viral Hepatitis, ed. Szmuness et al.

*Primary Examiner*—Blondel Hazel
*Attorney, Agent, or Firm*—Saidman, Sterne, Kessler & Goldstein

[57] ABSTRACT

A purified form of a DNA virus which has the following characteristics: molecular weight greater than $2 \times 10^6$ Daltons; substantial immunoreactivity towards an anti-HBsAg monoclonal antibody obtained from cell line ATCC HB 8058; substantially no immunoreactivity towards an anti-HBsAg monoclonal antibody obtained from cell line ATCC CRL 8018; concentration dependent immunoreactivity towards polyclonal IgG anti-HBsAg antibodies, which increases with increased concentration of said DNA virus; discrete particulate form when observed by immunoelectron microscopy in the presence of IgM antibodies from cell line ATCC HB 8058; the DNA of said virus showing hybridization with DNA from hepatitis B viral DNA; and said DNA virus showing, in chimpanzees, infectivity having the characteristics of non A, non B hepatitis.

13 Claims, 7 Drawing Sheets

NON-A, NON-B. HEPATITIS, VIRUS, METHODS OF IDENTIFICATION PURIFICATION, CHARACTERIZATION, DIAGNOSIS AND IMMUNIZATION

This application is a continuation of application Ser. No. 418,708, filed 9/16/82, abandoned.

BACKGROUND OF THE INVENTION

Part of the present invention was developed with funds obtained from the following sources: AG-04145, AA-02666, AM-17702, AM 17609, CA-32605, AM-07218, 1-K02-AA-00048, from the United States Government.

1. Field of the Invention

The present invention deals with the identification, isolation, characterization, purification and use of non A, non B hepatitis virus, as well as diagnostic methods and vaccine methods therefor.

2. Brief Description of the Prior Art

The name non A, non B hepatitis is given to acute and chronic cases of viral hepatitis in humans which occur in the absence of infection with any known or serologically identifiable virus associated with hepatitis B (HBV) or hepatitis A (HAV). The characteristics of non-A, non-B (hereinafter "NANB") hepatitis are well described in Dienstag et al, Chapter 302 of Harrison's "Principles of Internal Medicine", 9th Ed, McGraw-Hill Book Co., 1980), pp. 1459-1467, and by Robinson, W. S., "The Enigma of Non-A, Non-B Hepatitis", The Journal of Infect. Dis., Vol. 145 No. 3, pp. 387-395 (1982). These two articles are herein incorporated by reference, and the following comments are extracted therefrom.

Sensitive serologic tests for identifying both types A and B hepatitis have led to the identification of hepatitis cases with incubation periods and modes of transmission consistent with an infectious disease, but without serologic evidence of hepatitis A or B infection.

Transmission of the disease to chimpanzees has clearly established that many of the cases are caused by one or more infectious agents. There have been intensive efforts in many laboratories throughout the world in the past few years to identify and characterize agents that are responsible for these infections.

Clinical diagnosis of NANB hepatitis is made by excluding infection with known hepatitis viruses and other known factors that cause hepatitis. The infection occurs with high frequency after blood transfusion or parental drug abuse, in person to person contact and in other settings that are also associated with HBV infections. Endemic and apparently epidemic disease has also been observed without obvious overt parental transmission.

Despite these advances and intensive efforts to date, no etiologic agent of NANB hepatitis has been unequivocally identified as an antigenic ultrastructural or molecular entity. This result suggests that the concentration of viral antigen in the serum of patients with NANB hepatitis may be much lower than that of HBV antigen in patients with hepatitis B, or that appropriate reagents or methods have not been heretofore described to identify the virus, its proteins, or its genetic material.

The most important experimental advance in this field to date has been the transmission of NANB hepatitis agents to chimpanzees. This provided a direct demonstration of a transmissible agent, associated with NANB hepatitis, in an animal model of the disease (See, for example, Alter, H. J. et al, Lancet 1: 459-463 (1978), Tabor, E. et al, ibid 1: 463-466 (1978), Hollinger, F. B. et al, Intervirology 10: 60-68 (1978), or Bradley D. W. et al, J. Med. Virol. 3: 253-269 (1979), all of which are herein incorporated by reference).

Despite the fact that NANB hepatitis has been transmitted to experimental animals, no virus or other infectious agent(s) has been physically identified with certainty prior to this invention. Although detection of apparently unique antigen/antibodies systems in the sera of patients and chimpanzees with NANB hepatitis have been reported, the results have been difficult to confirm, and none of these tests has clearly identified sera known to contain NANB agents (see for example, Vitvitski, L. et al, Lancet 22: 1263-1267 (1979), Kabiri, M. et al, Lancet 2: 221-224 (1979), Tabor E., J. Med. Vol. 4: 161-169 (1979) and Chircu, L. V. et al, J. Med. Virol. 6: 147-151 (1980). In addition to antigen, virus-like particulate structures have been observed by electron microscopy in serum and liver of humans and chimpanzees infected with NANB hepatitis (see for example Bradley, D. W., J. Med. Virol. 3: 253-269 (1979) and Bradley, D. W. et al, J. Med. Virol. 6: 85-201 (1980)).

An evaluation of all of these studies has been made by Robinson, supra in J. Inf. Dis. Vol. 145, (1982) who stated that "Without more definitive evidence concerning these particles and because numerous investigators have failed to confirm these findings it is not possible at this time to conclude that any HBV-like virus is ever a cause of NANB hepatitis."

In view of all of the above, it is quite clear that there exists at present a great need to identify, isolate and characterize the etiologic agent(s) causative of NANB hepatitis. A need also exists for accurate and unambiguous identification and detection techniques therefor, which will help in the quick and accurate diagnosis of the disease.

SUMMARY OF THE INVENTION

It is therefore an object of the invention to provide an accurate and specific characterization of the etiologic agent of NANB hepatitis.

It is another object of the invention to provide for a method of identifying and detecting the etiologic agent of NANB hepatitis in samples.

Still another object of the invention is to provide for a method of diagnosing NANB hepatitis in animals.

Yet another object of the invention is to provide a vaccine against NANB hepatitis, and a method of immunization which comprises the use of such vaccine.

Still another object of the invention is to provide a method for the purification of NANB hepatitis virus.

These and other objects of the invention as will hereinafter become more readily apparent have been attained by providing:

A purified form of a DNA virus which has the following characteristics:

(1) molecular weight greater than $2 \times 10^6$ daltons;
(2) substantial immunoreactivity towards an anti HBsAg monoclonal antibody obtained from cell line ATCC HB 9801.
(3) substantially no immunoreactivity towards an anti HBsAg monoclonal antibody obtained from cell line ATCC CRL 8018;
(4) concentration dependent binding capacity towards polyclonal IgG anti-HBsAg antibodies, which increases with increased concentration of said DNA virus;

(5) discrete particulate form when observed by immunoelectron microscopy in the presence of IgM antibodies from cell line ATCC HB 9801.

(6) a polypeptide profile on sodium dodecyl sulfate polyacrylamide gels, when affinity purified with IgM antibody from cell line ATCC HB 9801, comprising bands at about 50,000, about 23,000 and about less than 20,000 molecular weight;

(7) the DNA of said virus showing partial sequence homology with hepatitis B virus DNA by molecular hybridization; and (8) said DNA virus showing, in chimpanzees, infectivity having the characteristics of non A, non B hepatitis.

Another object of the invention has been attained by providing a method of detecting the presence of non A, non B hepatitis virus in the sample of an animal which comprises (A) confirming the presence of said virus in said sample, and (B) distinguishing said virus from hepatitis B virus.

Another object of the invention has been obtained by providing a method of purifying NANB virus from an animal sample by immunoaffinity chromatography wherein the immunosorbent antibody is a monoclonal antibody having substantial immunoreactivity towards said NANB virus.

The present invention also provides vaccines and vaccination methods utilizing live, attenuated or inactivated forms of the NANB virus.

BRIEF DESCRIPTION OF THE DRAWINGS

The present invention will become better understood by reference to the accompanying description when interpreted in view of the following drawings, wherein.

BRIEF DESCRIPTION OF THE PREFERRED EMBODIMENTS

Figure 1:
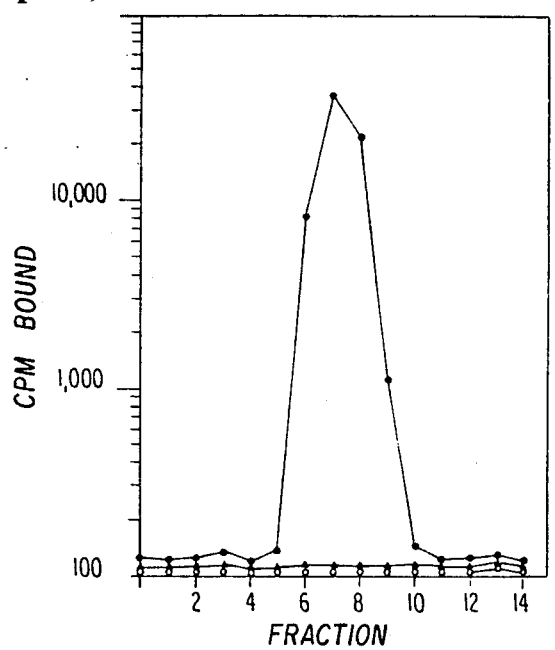
FIG. 1 is a representative example of binding activity isolated from human serum after elution of the monoclonal 5D3-IgM anti-HBs affinity column with glycine-HCl buffer (pH 2.6). Symbols are as follows: (●) CPM bound in the eluate by monoclonal 5D3-5D3 radioimmunoassay (RIA); (▲) CPM bound in the monoclonal assay on fractionated serum passed through the affinity column and eluted with Pi/NaCl; (■) binding profile of glycine. HCl eluate when analyzed by a commercial radioimmunoassay kit (polyclonal antibodies, AUSRIA II), See Example 1.

The present invention is based on the discovery of highly specific and accurate tests for the identification and characterization of the causative agent of non A, non B hepatitis. The inventors have made use of a variety of analytical techniques to characterize NANB hepatitis virus and distinguish the same from hepatitis virus A (HVA) and hepatitis virus B (HBV). These techniques include physical-chemical properties, immunological properties, genetic characterization and infectivity characterization.

The discovery of NANB hepatitis virus was made by detecting its presence in the blood of persons with the clinical signs of hepatitis but no serologic identification by any of the prior art immunoassay techniques using polyvalent IgG antibodies. A series of monoclonal antibody screening tests were then developed with alternatively positive and negative binding for various different monoclonal antibodies, which can readily characterize and detect NANB virus and distinguish the same from hepatitis B virus.

In the discussions that follow, mention is made to a number of antibodies, both monoclonal and polyvalent. For clarity purposes and reference, the following summarizes the nature, origin and type of these antibodies:

(1) 5D3: Represents a monoclonal IgM antibody against HBsAg, obtained from hybridoma 5D3 on deposit at the ATCC with deposit number HB 9801. Reference is made to this antibody in U.S. Pat. No. 4,271,145 to Wands et al, as well as in Wands et al, Proc. Nat. Acad. Sci., USA Vol. 78: 1214–1218, Feb. 1981, both of which are herein incorporated by reference.

(2) 3D4: Represents a monoclonal IgM antibody having specificity against HBsAg (i.e. anti-HBsAg), obtained from cell line 3D4 on deposit at the ATCC with deposit number HB-8170.

(3) 1F8: Represents a monoclonal IgM anti-HBsAg antibody derived from cell line 1F8 on deposit at the ATCC have deposit number CRL 8018. This antibody is described in the aforementioned Wands et al U.S. Pat. No. 4,271,145 and Wands et al PNAS Vol. 78, Feb. 1981 paper.

(4) 5C11: Represents a monclonal $IgG_1$ anti-HBsAg antibody obtained from cell line 5C11 deposited at the ATCC with deposit number HB-8171.

(5) AUSRIA II: Represents antibodies from a commercially available HBsAg test kit (Abbott) containing polyclonal IgG antibodies.

These and other mentioned antibodies are also described in one or both of the following copending U.S. Pat. applications: Ser. No. 188,735, filed September 19, 1980 to Wands, Zurawski and Ser. No. 533,161 filed Sept. 19, 1983, a continuation of Schoemaker, for "Immunoassay Utilizing Monoclonal High Affinity IgM Antibodies"; and Ser. No. 372,530, filed Apr. 28, 1982, to Wands and Zurawski, by the same title, both of which are also herein incorporated by reference.

Also, a bacterial culture containing a recombinant plasmid with HBV-DNA sequences, pAO1 HBV is on deposit with ATCC Number 31873.

The NANB virus can be isolated from either a human or other animal host, e.g., chimpanzee, marmoset, and other suitable hosts for NANB virus, which is infected with NANB hepatitis. The presence of the NANB virus has been implicated in the prior art by excluding identifiable hepatitis viruses (HAV, HBV, Epstein-Barr virus, cytomegalovirus and others) and other etiologic factors (for example, hepatotoxic drugs and chemicals). Exclusion of other viruses mentioned above can still be used to suggest but not establish the presence of the NANB infectious agent in the host. However, with the advent by the present invention of highly specific tests for NANB virus it is preferred to utilize these, see infra.

Preferably, affinity chromatography using monoclonal 5D3 IgM anti-HBs can be utilized for the purification and subsequent characterization of the antigen composition. A suitable material is obtained by coupling 5D3 to Sepharose 6B®. Serum from an appropriate host is placed in contact with the monoclonal antibody on the solid phase support and the material is incubated for several hours at room temperature. The supports are then extensively washed with an appropriate physiological buffer (e.g., PBS-phosphate buffer saline) at a physiological pH. Column fractions can then be collected with an acidic buffer (for example pH 2–3). The pH of each fraction is adjusted to physiological pH, and binding activity is determined with the appropriate antibodies. Peak fractions exhibiting the highest binding activity can then be pooled to collect the NANB virus. Virus can also be isolated from the supernatant of any cell culture (e.g., bacteria, yeasts and other eukarotic cells infected with said virus or viral DNA) or fermentation broth producing the same.

The NANB virus can be characterized and identified by at least four different characteristics, each of which is described in turn hereinbelow.

Physical-chemical characteristics.

NANB virus has a molecular weight of approximately $2 \times 10^6$ as determined by Sepharose 4B® chromatography. The virus appears as distinct particles by immunoelectron microscopy. When the virus is isolated from serum by the 5D3-IgM affinity chromatography described above, prominent spiculated particles at 220,000× are observed, suggesting the presence of 5D3 anti-HBs on their surface. When affinity purified material is applied to sodium dodecyl sulfate 10% polyacrylamide gels and compared to HBsAg virus it is seen that there are similar polypeptides in all specimens at a molecular weight of about 50,000 and at molecular weights of 22,000–23,000. In addition, however, NANB virus shows three additional major protein bands not observed in HBsAg, one has a Mr of approximately 80,000 and, of the two others, the first has a molecular weight slightly greater than 23,000 and the second has a molecular weight less than 20,000. (See FIG. 3).

Immunological characteristics.

NANB virus reacts with some monoclonal antibodies having specificity, i.e., immunoreactivity, for distinct HBsAg-related epitopes, and not with other such anti-HBsAg monoclonal antibodies. For example, NANB will cross react at all concentrations with antibody 5D3 or with antibody 3D4 (both of which are monoclonal IgM anti-HBsAg antibodies). On the other hand, NANB will not cross-react with antibody 1F8 (also a monoclonal IgM having specificity against HBsAg) or with monoclonal 5C11 (a $IgG_1$ antibody). This serves to clearly distinguish NANB virus from hepatitis B virus, which reacts with these monoclonal antibodies. Immunoreactivity of NANB with polyvalent anti-HBs antibodies (commercially available AUSRIA II) is concentration dependent. At concentrations of about 1 ng to 100 ng, the polyvalent IgG antibodies do not detect or bind the NANB virus. Upon concentration of NANB by about 100 fold or larger than these, binding and detection by polyvalent IgG can be observed. However, in some instances, polyvalent anti-HBsAg antibodies do not detect or bind to NANB hepatitis serum even after enrichment by affinity chromatography and 100 fold concentration as described above. Preincubation of NANB with 5D3 anti-$HB_s$ at these higher concentrations blocks the binding by conventional polyvalent anti-HBs.

Genetic Characteristics.

The DNA sequence of NANB virus is partially homologous related but not identical to HBV-DNA. It can thus be detected by hybridization with a purified HBV-DNA probe. See, infra.

Infectivity Characteristics

NANB virus having the above physico-chemical, morphological, immunologic and genetic characteristics is infectious. Infectivity studies of viral hepatitis are positive in chimpanzees and in man. The characteristics for the infection are different than those normally seen for HBV or HAV. The incubation period, as defined from inoculation of infectious material to the appearance of virus or viral protein in the blood, is longer than previously recognized. Alanine aminotransferase (ALT) elevation precedes the appearance of antigenemia by several weeks. Antigenemia may occur in the absence of ALT elevations, a phenomenon observed in man. A chronic viral carrier state in man and chimpanzees may occur. The period of antigenemia and/or viremia appears to persist for weeks to months and usually disappears with recovery. Antigenemia is still detectable in the resolution phase of illness when ALT levels are normal, a similarity to HBV infection in man. Several episodes of antigenemia may occur during the course of infection. Pre-existing anti-HBs is not protective in the animal, confirming that NANB virus is sufficiently different in antigenic composition from HBV. (See FIGS. 6, and 8-10).

It should be noted, of course, that the aforementioned characteristics are but only one possible set. Obviously, as more of these characteristics are researched and discovered it may be possible to characterize the virus, for example, by additional monoclonal antibodies, or DNA probes including one or more that do not cross react at all with hepatitis B. This possibility, however, is fully contemplated in the present application which, when pertaining to the virus per se, is meant to cover the virus itself regardless of any additional or even novel identifying tests.

The NANB virus characteristics can be used to develop highly sensitive and accurate tests for detecting the presence of NANB virus in animal samples, such as blood—especially blood to be transfused-, serum, urine, milk, tissue samples, feces, and the like. Particularly useful is the detection of NANB virus in animal serum, especially human serum, and products derived from human blood, such as red blood cells, plasma, platelet concentrates, clotting factor concentrates and the like, for the diagnosis of NANB hepatitis. Also particularly useful is the detection of NANB virus in samples of blood from blood donors, to screen for the possibility of transmission of NANB hepatitis infection to recipients.

The availability of purified NANB virus allows for the development of immunoassay methods and systems. Any appropriate antibodies can be used in any of the multiple immunoassay procedures currently available to the art (see for example, T. Chard "An Introduction to Radioimmunoassay and Related Techniques", North-Holland 1978, or Schuurs, A. H. W. M, et al, "Enzyme Immunoassay", Clin. Chim. Acta 81: 1-40 (1977), both of which are herein incorporated by reference). For example, the presence of the virus in a sample can be detected by radioimmunoassay, enzyme immunoassay, or latex agglutination immunoassay. The technique utilized can be competitive, "sandwich" (forward, reverse or simultaneous), double antibody, or enzyme cascade, all of which are well known to those of skill in the art. It may be useful for certain techniques to prepare, by art known methods, detectably labeled NANB virus such as NANB labeled with a radiolabel ($I^{125}$, $C^{14}$, $H^3$, $P^{32}$, etc.), with an enzyme (alkaline phosphatase, peroxidase, etc.) with a fluorescent probe, and the like. The antibodies can be either in solution or immobilized, such as for example, on the inside of tubes, on polymer or glass beads, on plastic strips, and the like.

Detection can also be carried out by hybridization analysis using a detectably labeled probe. The genetic information or code of a specific virus comprises a nucleic acid which may be composed of a polymer of ribonucleotides (RNA) or deoxyribonucleotides (DNA). It is known that nucleotide molecules that are complementary to one another can interact in solution by "hydrogen-bonding" to form stable base pairs. Thus, adenine recognizes thymidine and guanine recognizes cytosine. When two single-stranded, complementary, DNA molecules are present in a solution under conditions in which the complementary nucleotides can recognize one another, these molecules will interact to form a stable duplex structure. This duplex is resistant to attack by certain nucleases which totally degrade single-stranded DNA. It is therefore possible to ascertain with great precision the extent of duplex formation. This interaction of base sequences in polynucleotides reacting in solution is referred to as "reannealing" or "molecular hybridization" and can be performed under specific and sensitive conditions in which false interactions do not occur.

For substantially stable and recognizable hybrids to be formed, minimum complementary sequence lengths of approximately 50-100 nucleotides or more often 100-200 nucleotides are required. The ability to form such hybrids appears to depend on the experimental conditions of the hybridization reaction (ionic strength, polarity, pH and temperature of the hybridization solution), the concentration of the complementary nucleic acid molecules and the length of time of the incubation. Another variable in the reaction is the physical state of the DNA in the test sample, in that it can be in solution or fixed to a solid support matrix such as a nitrocellulose filter paper. In the latter case, the rate of hybridization between the detecting probe and the test sample of DNA affixed to the solid support surface is slowed by approximately 30%. The latter method is, however, extremely sensitive for detection of hybridizing sequences and with a [$^{32}$P] radioactively labeled DNA probe of specific activity 2-4 $\times 10^8$ cpm per $\mu$g DNA, as easily obtained by workers skilled in the art, a 2-5 mm diameter circular spot on a nitrocellulose filter containing 0.1 pgm ($10^{-13}$ gm) of specific DNA sequence or less can be detected.

Depending on the various factors mentioned above, the hybridization reaction can be performed under very stringent conditions, so that a perfect or near perfect match in complementary DNA sequence is required or under less stringent conditions in which only a partial match is required. As the conditions for stringency of hybridization are relaxed, nucleic acid molecules of lesser and lesser sequence homology will form hybrids. This, of course, decreases the specificity of the reaction and raises the chances of false positive results. Therefore, in the preferred embodiment, hybridization conditions of high stringency have been used, so that only molecules with sequence regions of approximately 100-200 nucleotides or more in common with or nearly identical to HBV-DNA will form stable and detectable hybrids on a nitrocellulose filters. This enables the use of the hybridization method to identify DNA molecules in any cell, tissue, tissue extract, serum, plasma, body fluid, secretum, semen, breast milk, vaccine or the like, containing DNA molecules or genetic information closely related, nearly identical or identical to NANB-DNA.

As disclosed in this invention, NANB hepatitis virus(es) contain sequences closely related to HBV-DNA and can be detected by hybridization with a purified and suitably labeled HBV-DNA probe. DNA or RNA molecules which are not closely related to HBV-DNA will not be identified or detected by this method. These methods, considerations and conditions as well as many variations in hybridization technology as well as means to detect, isolate and identify hybrids are well known to those skilled in the art. Details concerning the preparation of the recombinant HBV-DNA probe, the labeling of the probe, the hybridization conditions are described in Chakrabarty et al, Nature, Volume 286, No. 5772, pages 531-533, July 31, 1980; Shouval et al, Proceedings National Academy of Science (PNAS) U.S.A., Volume 77, No. 10, pages 6147-6151, Oct. 1980; Shafritz and Kew, Hepatology, Volume 1, No. 1, pages 1-8, Jan.-Feb., 1981; Shafritz, D. A. et. al, New Engl. J. Med., 305:1067-1073, 1981; and copending U.S. patent application Ser. No. 249,369, filed Mar. 31, 1981 entitled Diagnostic Test for Hepatitis B Virus; now U.S. Pat. No. 4,562,159 all hereby incorporated by reference.

Regardless of the technique(s) used, the detection of the virus in a sample is carried out by an overall two step test, which not only serves to confirm its presence but also distinguishes it from HBV, with which it is closely related.

For example, the detection test can comprise a first step of testing for immunoreactivity with an antibody such as 5D3 or 3D4, with which NANB virus is reactive, followed by a second step of immunoassay with an antibody such as 5C11 or 1F8 with which NANB virus is not cross reactive, but HBV is.

Another two step test comprises a first immunoassay step using an antibody such as 5C11 or 1F8 (showing no cross reactivity), followed by DNA hybridization using an HBV-DNA or an NANB-NA (see infra) detectably labeled probe (e.g., $^{32}P$ or biotin-labeled probe).

An alternative test is a two step methodology wherein the first step is an immunoassay with 5D3 or 3D4 monoclonal IgM, followed by studying the infectivity characteristics in chimpanzees.

Alternatively, a two step analysis can be used with the first step being an immunoassay with 5D3 and in a second step a polyacrylamide gel on sodium dodecyl sulfate seeking the differential proteins present in NANB and not present HBsAg.

There are obviously other possibilities, such as procedures utilizing more than two steps, for example, screening with 5D3, 3D4, 5C11, 1F8, testing for hybridization with a DNA probe, and infectivity characteristics. The two step test, (in any desired order) however, is a minimum, in order to distinguish over the possibility that the samples may be infected with HBV.

Lack of cross reactivity with polyvalent IgG anti-HBsAg is also indicative of the presence of NANB virus and can be added to the battery of the aforementioned tests. It is however, not conclusive evidence since positive identification such as concentration of antigen is still needed to confirm its presence.

The invention lends itself to the preparation of kits useful in the diagnosis of NANB hepatitis. For example, such a kit may comprise a carrier being compartmentalized to receive one or more container means therein, including a first container containing a monoclonal IgM antibody having immunoreactivity towards said NANB virus; and a second container containing a monoclonal antibody having immunoreactivity towards HBsAg but no immunoreactivity towards the NANB virus.

The kit may also comprise a third container means containing detectably labeled HBV-DNA probe, and/or additional container means containing another monoclonal antibody having immunoreactivity towards HBsAg but no immunoreactivity towards the NANB virus.

Detectably labeled HBV-DNA may also be present in the kit in another container.

The use of hybridization techniques initially with purified cloned HBV-DNA can be utilized to clone the DNA of NANB hepatitis viruses with partial sequence homology to HBV-DNA. This is based on the finding that even under very stringent hybridization conditions, the HBV-DNA probe is capable of detecting NANB virus in both human and chimpanzee serum. With purification of the virus by the monoclonal antibody affinity column described herein, the DNA of the virus can be extracted and cloned in bacterial plasmids such as pBR 322 or bacteriophages such as bacteriophage λ.

A series of restriction endonucleases are used to cleave the DNA into specific segments with known specific 5' and 3' ends by recognition of specific hexanucleotide sequences in double-stranded DNA. These DNA fragments can then be introduced into plasmids or bacteriophages treated with the same restriction enzymes to produce chimeric recombinant DNA molecules. These recombinant DNA molecules are introduced into *E. coli*, amplified and produced in large amounts. Recombinants containing NANB virus DNA sequences related to HBV-DNA are identified by molecular hybridization using standard screening procedures. A large group of such clones can then be used to find additional clones with NANB virus sequences only slightly related to HBV-DNA. By this approach, the entire molecular structure of NANB hepatitis virus(es) can be reconstructed. With this information and these clones, new recombinant DNA clones can then be prepared which are unique for NANB hepatitis virus(es).

The availability of purified isolated NANB virus, substantially free of cellular components and other viral or non-viral components, allows for the preparation of an NANB vaccine. The vaccine can be prepared according to a number of well known methods in the art. Thus, a vaccine can be prepared from the whole live virus or from immunologically active but non-pathogenic subcomponents thereof, such as capsids and the like, obtained by splitting with enzymes or solvents. Chemically attenuated live or killed viral vaccines can also be used, for example, by the treatment of virus with propio lactone, dilute formalin(i.e., conc. less than 1%), ethylene amine, halogenated hydrocarbons, and the like. These agents decrease virus pathogenicity while allowing the material to retain immunogenicity.

Another technique for attenuating the virulence of the virus is to develop an avirulent or slow growing strain, or a mutant incapable of sustained replication in the host. This is generally known in the art as "genetic attenuation", and can be done by genetic manipulations or by serial passage. For example, the production of live attenuated viruses can be carried out by adapting the isolated virus to cultures containing tissue cells and attenuation for example by 10-200 passages in such cultures, after which said viruses multiply and a vaccine is then prepared. Another method of producing live vaccine is to select and culture clones. If the infected cells are used for the production of the live vaccine, it is advantageous to release the virus from the cells. Techniques for preparing vaccines are generally detailed in a publication such as "Newcastle Disease Vaccines: Their Production and Use", Allan, W. H., J. E. Lancaster and B. Toth; Food and Agricultural Organization, Rome 1978.

The vaccines, whether live or attenuated, in their many different forms, can be prepared in suspension in a manner known per se with a pharmacologically acceptable vaccine carrier, such as a bio-acceptable oil. It is advantageous to add thereto a stabilizer, particularly if a dry preparation is prepared by lyophilization. An adjuvant such as aluminum hydroxide may be added. The stabilizing agent can be a carbohydrate such as sorbitol, mannitol, starch, dextran or glycose; a protein like albumin or casein; a protein-containing agent like bovine serum or skim milk, and a buffer such as an alkaline metal phosphate. 1–100 µg of virus can normally be present in such composition per unit dosage.

The vaccine can be administered to animals, especially humans, to prevent the same from developing NANB hepatitis. Vaccines (1–100 µg of antigen) may be administered intramuscularly followed by 2nd, 3rd and even more boosts at 2 two month intervals. It should be noted that vaccines may be given subcutaneously or intravenously and the route of administration, dosages, and time between primary immunization and secondary boosts will depend on the immunogenicity and characteristics of the viral antigens employed.

Having now generally described this invention, the same will become better understood by reference to certain specific examples which are included herein for purposes of illustration only and are not intended to be limiting of the invention unless otherwise specified.

EXAMPLE 1

Monoclonal IgM Radioimmunoassay for Hepatitis B Surface Antigen: NANB-Binding Activity in Serum that is Unreactive with Polyvalent Antibodies

MATERIALS AND METHODS

Patients. Patient A was a 26-year-old man with acute hepatitis (AH). At the time of study the serum glutamic-oxaloacetic transaminase (SGOT; asparate aminotransferase) was 2161 international units (IU)/ml (normal <50), bilirubin was 9.2 mg/100 ml (normal <(1.0), and alkaline phosphatase was 119 IU/liter (normal <45). His disease resolved over 2 months. Patient B was a 65-year-old man with chronic active hepatitis (CAH). He developed AH 2 months after multiple transfusions for gastrointestinal hemorrhage due to a duodenal ulcer. Liver biopsy showed a histologic pattern consistent with acute viral hepatitis with submassive necrosis. The patient improved, with SGOT, bilirubin, and alkaline phosphatase values returning to normal over several weeks. However, 2 months later he was again icteric and symptomatic; liver biopsy showed CAH with postnecrotic cirrhosis. For the last 4 years his disease has remained active, with SGOT values ranging between 45 and 221 IU/ml, with mildly increased alkaline phosphate levels. Patient C was a 42-year-old woman blood donor. Her physical examination and SGOT bilirubin, and alkaline phosphatase were normal. Patient D was a 58-year-old man with HBsAg-positive CAH proven by liver biopsy. Patient E was a 36-year-old man with AH. The SGOT was 650 IU/ml, bilirubin was 2.4 mg/100 ml, and alkaline phosphatase was 121 IU/liter at the time of study.

Patient E had no serologic markers for hepatitis A or B [negative for HBsAg, antibodies to hepatitis B core antigen (anti-HBc), anti-HBs, and IgM antibodies to hepatitis A antigen (anti-HA); tested by Abbott RIAs] during the acute phase of his disease. Patient A was positive for anti-HBc and anti-HBs but negative for HBsAg and IgM anti-HA. Patient B was also negative for HBsAg anti-HBs and IgM anti-HA during AH. However, after the development of CAH he became positive for anti-HBc and anti-HBs but not HBsAg and remained seropositive for these antibodies for the last 4 years in the setting of active liver disease. He was negative for anti-HA IgM. Patient C had no serologic markers for hepatitis A or B. Patient D was positive only for HBsAg and anti-HBc.

Patients A, B, C and E were selected for more detailed study because of the high binding activity exhibited by their serum in a 5D3—5D3 monoclonal sandwich RIA. It should be noted that patient B serum was highly positive in the RIA during AH and CAH and he was consistently identified by the assay under code. Patient C was of special interest; her blood was considered to have transmitted acute hepatitis with no serologic markers of hepatitis B or A. Ten units of blood were transfused to the recipient and under code her serum was the only one of the eight units available for study that was reactive in the monoclonal assay. Patient D was selected as a control because his serum was highly reactive for HBsAg with both the monoclonal RIA and commerical RIA (AUSRIA II, from Abbott).

Affinity Purification. Studies were performed to isolate from serum the high binding activity detected in the 5D3—5D3 monoclonal RIA. Affinity columns of monoclonal 5D3 IgM anti-HBs were prepared by coupling 2–4 mg of IgM per ml of cyanogen bromide-activated Sepharose 6B ®. Serum (20–50 ml) from each patient was placed over the columns and incubated for several hours at room temperature; the columns were then extensively washed with phosphate-buffered saline ($P_i$/NaCl) (pH 7.2). Subsequently, 1- to 2-ml fractions were collected by elution with glycine HCl buffer (pH 2.6). The pH of each fraction was adjusted to 7.4 with 0.1M NaOH and the binding activity was determined on the eluates by the monoclonal and AUSRIA II RIAs. Peak fractions exhibiting the highest binding activity were pooled and concentrated approximately 100-fold by the Micro-ProDiCon device (Bio-Molecular Dynamics, Beaverton, Ore.) for further studies as outlined below.

Immunoelectron Microscopy. Serum samples (3–5 ml) and 5D3-affinity-purified material from the patients with acute or chronic hepatitis, and serum from normal patients and liver disease controls (individuals with halothane hepatitis, alcoholic hepatitis, or primary biliary cirrhosis who were unreactive in the conventional monoclonal RIA) were incubated for 12 hr at 4° C. with 100 µg of 5D3 IgM purified by Sepharose 4B chromatography. The incubation mixture was centrifuged at 12,000×g for 1 hr, the supernatant was decanted, and the precipitate was resuspended in 30 µl of $P_i$/NaCl. Drops (5–10 µl) were applied to colloidion/carbon-coated specimen grids, negatively stained with 2% potassium phosphotungstate (pH 7.2), and examined with a JEOL 100B electron microscope. Additional controls consisted of serum and 5D3 affinity-purified material incubated with 100 μl of serum having an anti-HBs titer of 1:500,000 by passive hemagglutination. The latter serum was obtained from a multi-transfused hemophiliac.

Antigenic Characterization. In order to further define the antigenic composition of the 5D3 binding material a series of RIAs employing monoclonal IgG and IgM anti-HBs antibodies were developed. In brief, 5D3 IgM anti-HBs was coupled to a solid-phase support, followed by the addition of serial dilutions of serum samples or 5D3 IgM affinity-purified material and 125I-labeled IC7 and 5C3 (IgG1 and IgG2a monoclonal anti-HBs), 2F11, 1F8 and 5D3 (IgM monoclonal anti-HBs). The reaction mixture was incubated for 4 hr at 45° C. and then the solid-phase support was washed with distilled water. Radioactivity (cpm) bound was determined with a Packard gamma counter. The monoclonal antibodies employed in the RIAs were shown to recognize different determinants as demonstrated by the absence of competitive inhibition in HBsAg binding studies [Wands, Jr. et al, Lancet 1:May, 1982 incorporated by reference]. The binding activity exhibited by the samples in the monoclonal RIAs was also compared to that observed with conventional anti-HBs reagents (AUSRIA II). Finally, the 5D3 affinity-purified material was concentrated approximately 100-fold as described above and retested with the AUSRIA II assay. Under these conditions, the NANB antigen became reactive.

Analysis of Polypeptides. Binding material (20–25 μl) prepared by affinity chromatography from patients was applied to NaDodSO$_4$/10% polyacrylamide gels (Moriarty et al ibid, 78: 2606 (1981)). Sepharose 4B column-purified 5D3 IgM anti-HBs served as control. Therefore, the polypeptide profiles on the gels of the affinity-purified material derived from patients A, B and C and the HBsAg-positive patient were compared with CAH (patient D).

Molecular Weight Determination. Experiments were performed to determine the approximate molecular weight of the 5D3-binding material. Serum samples (10–15 ml) from patients B and C were placed over Sepharose 4B columns and eluted with P$_i$/NaCl. The molecular weight markers were blue dextran, IgM, IgG and myoglobin. Aliquots of the fractions were tested in the 5D3—5D3 monoclonal RIA and the binding activity was compared to the elution profiles of the molecular weight markers. The fractions exhibiting the highest binding activity were pooled, concentrated, and immunoprecipitated with 5D3 as noted above and examined by electron microscopy.

RESULTS

FIG. 1 depicts a typical binding profile of the various fractions eluted from the 5D3 IgM anti-HBs affinity columns as measured by the 5D3—5D3 monoclonal RIA. Binding activity was recovered from serum after elution with glycine HCl buffer and, as can be seen in Table 1, the amount of radioactivity bound in the peak fractions was higher than that obtained in the unfractionated serum.

TABLE 1

Antigenic characterization of 5D3 binding activity by polyvalent anti—HBs reagents

| | Binding, cpm | | | | | |
|---|---|---|---|---|---|---|
| | Serum* | | 5D3 affinity purified+ | | Concentrate‡ | |
| Patient | 5D3-5D3 | AUSRIA II§ | 5D3-5D3 | AUSRIA II§ | 5D3-5D3 | AUSRIA II§ |
| A | 15,215 | 142 | 34,162 | 121 | 72,510 | 8216 (56) |
| B | 5,610 | 128 | 22,300 | 118 | 66,721 | 4432 (42) |
| C | 8,126 | 142 | 34,136 | 102 | 54,613 | 2167 (71) |
| D | 22,416 | 20,618 (11,210) | 46,198 | 26,210 (12,617) | — | — |
| E | 34,259 | 137 | — | 735 | — | 5792 (117) |

*One hundred microliters of serum tested in the simultaneous 5D3-5D3 monoclonal or AUSRIA II RIA. Results are positive if the cpm bound are greater than 210 or 350, respectively.
+Binding activity isolated from 30–50 ml of serum by affinity chromatography. In each RIA, 100 μl was tested.
‡Peak binding fractions (see FIG. 1) were pooled (5–7 ml) and concentrated to 50 μl by Micro-ProDiCon. In each RIA, 10 μl was tested.
§The numbers in parentheses represent the values obtained in AUSRIA II after a 12-hr preincubation with purified 5D3 IgM monoclonal anti—HBs.

No binding activity was observed with conventional polyvalent anti-HBs reagents. Furthermore, the fractionated serum was devoid of binding activity after passage over the columns and elution with P$_i$/NaCl as measured by the monoclonal RIA. (FIG. 1)

Figure 2:
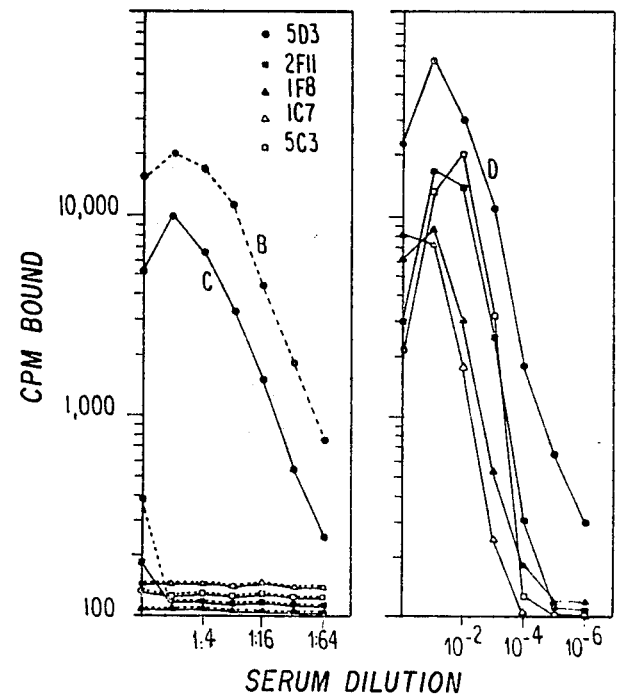
FIG. 2 shows the binding profiles exhibited by five monoclonal RIAs in human serum derived from three patients (See Example 1). All monoclonal RIA antibodies are reactive with serial dilutions of serum and indicate that such IgG and IgM monoclonal anti-HBs recognize determinants present on HBsAg (patient D) (Right). In contrast, only the 5D3-5D3 monoclonal assay shows high binding values in serial dilutions of serum from patients B and C (left). Description and characterization of the monoclonal antibodies is given in the text, infra.

Some of the antigenic characteristics of the 5D3-binding material were determined in this Example. (See also below). In one study five monoclonal RIAs were employed as shown in FIG. 2. FIG. 2 Right is a semilogarithmic plot of the binding profile with serial dilutions of serum tested in RIAs using the monoclonal IgM and IgG anti-HBs antibodies (5D3, 2F11, 1F8, 1C7 and 5C3). All immunoassays showed high reactivity in the patient with HBsAg-positive CAH. In contrast, only the 5D3—5D3 RIA identified serum from patients B and C as positive, as shown by the absence of significant binding activity when the four other monoclonal RIAs were used (FIG. 2 Left). These findings indicate that the reactivity of these sera in 5D3—5D3 assay was the result of a specific antigen-antibody interaction and not just due to nonspecific binding of serum to murine monoclonal IgG and IgM anti-HBs.

Additional antigenic properties of the 5D3-binding material are also shown in Table 1. The degree of binding activity increased in the 5D3—5D3 assay as the serum samples from patients A, B and C were affinity purified and further concentrated. It is of interest that when all four specimens were concentrated approximately 100-fold (by volume) they showed strongly positive results with the polyvalent anti-HBs reagents (AUSRIA II). However, this binding activity was blocked by preincubation of these samples with 5D3 monoclonal anti-HBs. In contrast, only a 50% blockage of known HBsAg binding activity was observed in AUSRIA II after preincubation of affinity-purified HBsAg from patient D with 5D3 IgM anti-HBs.

Figure 3:
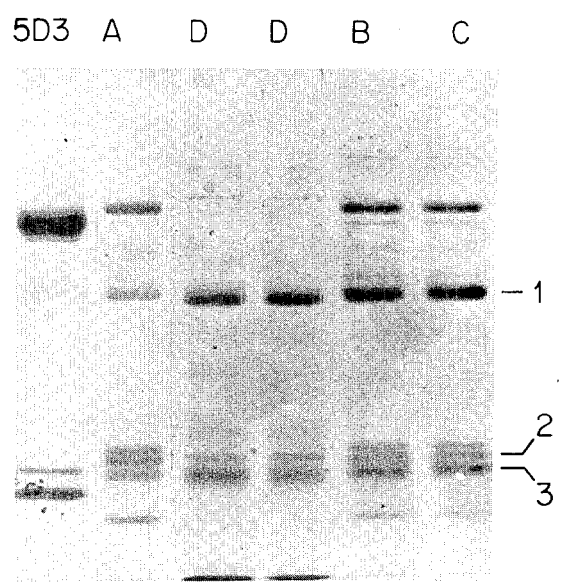
FIG. 3 shows the polypeptide profile on sodium dodecyl sulfate/polyacrylamide gel of the affinity purified material from patients' serum (Example 1): Patient A, acute hepatitis; Patient B, chronic active hepatitis; Patient C, blood donor; and Patient D, HBsAg-positive chronic acute hepatitis. There are three similar polypeptides in all four specimens (noted as 1, 2 and 3). Polypeptide 1 has a $M_r$ of 50,000 and polypeptides 2 and 3 have $M_r$s of 22,000–23,000. In Sample D there is a polypeptide of $M_r$ 27,000–30,000. However, in Samples A, B, and C there are three additional majors protein bands not observed in Sample D; one has a $M_r$ of approximately 80,000 (compared with 5D3 heavy chain) and of the two others, the first has a $M_r$ slightly greater than 23,000 and the second a $M_r$ less than 20,000. The heavy and light chains of the 5D3 antibody do not comigrate with any other proteins from Patients A, B, C and D.

The polypeptide profiles of the affinity-purified material from four patients on NaDodSO$_4$/polyacrylamide gels were compared, as shown in FIG. 3. Some striking similarities in protein bands were observed when comparisons were made among patients A, B, C, and HBsAg derived from patient D. A major 50,000-dalton protein was found to be common to all specimens, although the HBsAg polypeptide migrated slightly ahead of the other 50,000-dalton proteins from patients A, B, and C. Two other polypeptides in the 22,000- to 23,000-dalton range appeared to be common components in all four isolates. More importantly, the polypeptide profiles were identical in samples A, B, and C and, although there were some similarities to the polypeptides of HBsAg, as a group there were distinct differences as well.

Finally, the molecular weight of the binding material was approximately $2 \times 10^6$ in patients B and C as determined by Sepharose 4B ® chromatography.

Discussion

This Example shows a study which was designed to compare directly the properties of the binding material detected only in the monoclonal RIA and not in conventional assays (AUSRIA II). If the binding activity measured with the monoclonal RIA was identical to HBsAg, it would have been expected that the conventional assays should also yield positive results in view of the known sensitivity of the monoclonal RIA for HBsAg (100 ±30 pg/ml). The goal of the present study was to assess the relationship, if any, of HBsAg to 5D3 affinity-purified material derived from patients negative in the serum for HBsAg by conventional RIA with AH or CAH, and from a donor whose blood was implicated in transmitting AH to a recipient.

There is no doubt that the monoclonal 5D3 anti-HBs recognized a determinant on HBsAg as shown by the present study and previous observations (Wands et al, PNAS, 78: 1214–1218 (1981)). HBsAg was isolated from serum by the 5D3 IgM affinity column. The immunoreactivity of the isolate was confirmed by the high binding activity measured both in the 5D3 monoclonal and AUSRIA II assays. In addition, when affinity-purified HBsAg was preincubated with 5D3 IgM anti-HBs and the immunoprecipitate was examined by electon microscopy, typical 22- to 25-nm particles were observed. Clumping of the particles and their "spiculated" or "fuzzy" appearance is consistent with the presence of antibody on the surface. Indeed, this observation provides morphologic evidence of the interaction of the 5D3 monoclonal anti-HBs with a specific determinant(s) on HBsAg. The polypeptide profile on NaDodSO$_4$/polyacrylamide gels of the affinity-purified HBsAg isolate was consistent with previous reports demonstrating a major 50,000-dalton polypeptide and two smaller proteins (23,000 and 27,000 daltons). Finally, the immunoreactivity of the HBsAg isolate was further established by high binding activity in RIAs using the other four monoclonal IgM and IgG anti-HBs antibodies and conventional (commercially available polyvalent anti-HBs AUSTRIA II).

Some similarities were observed between HBsAg and the 5D3 immunoreactive material (NANB) isolated from patients A, B, C, and E. First, the binding activity recovered from serum by using 5D3-IgM anti-HBs affinity columns and the radioactivity bound in the eluate as measured by the monoclonal RIA was several-fold higher than that measured in serum. Furthermore, concentration of the eluate followed by retesting in the monoclonal RIA yielded even higher binding values. Second, immunoprecipitation of the affinity-purified material revealed distinct particles by electron microscopy. However, no particles were observed in the isolates after the addition of high-titer anti-HBs. The appearance and the size of the NANB particles was similar but not identical to HBsAg. The density of particles on electron microscopic grids was generally less than that observed with the 5D3-HBsAg immunoprecipitate. It should be noted be noted that, as with the 5D3-HBsAg immunoprecipitate, clumping of particles was observed, which presumably represents the presence of 5D3 antibody on their surface. Finally, as shown in FIG. 3, NaDodSO$_4$/polyacrylamide gel electrophoresis revealed three polypeptides in the same molecular weight range as previously described for HBsAg.

Although the 5D3 IgM anti-HBs binding material (NANB) shared certain properties with HBsAg, distinct differences were noted. These differences were most evident when the antigenic characteristics of the 5D3 immunoreactive material were examined by using other monoclonal IgG and IgM anti-HBs antibodies as well as conventional reagents. Four other monoclonal IgM and IgG anti-HBs antibodies were unreactive with 5D3 binding material when tested in solid-phase RIAs. In contrast, all four antibodies were highly reactive with HBsAg in the same RIAs. In this regard, it is noteworthy that 5D3 was coupled to the solid-phase support and the other $^{125}$I-labeled monoclonal IgM and IgG anti-HBs served as the indicator probes. It is likely, therefore, that the 5D3 binding material was bound to the solid-phase support but was not detected with the RIAs, suggesting that those epitopes were absent or were not available in sufficient concentration to be identified by the other monoclonal anti-HBs.

Additional examination of the antigenic characteristics of the 5D3-affinity-purified material was performed after concentration of the eluate (approximately 100-fold by volume). After each concentration all these isolates were reactive in AUSRIA II. More importantly, preincubation with 5D3 anti-HBs blocked the binding by the conventional anti-HBs. One possible interpretation is that the conventionally prepared anti-HBs reagents contain small amounts of an antibody like 5D3 IgM anti-HBs or of an antibody of the IgG class that competes for the same epitope. However, these isolates (Table 1) possessed high binding values with conventional anti-HBs in commercial RIAs, which suggests some antigenic crossreactivity of the determinants on HBsAg and the NANB 5D3 binding material. In contrast, preincubation of 5D3 with HBsAg resulted in an approximately 50% reduction in binding activity when retested by AUSRIA II. This result was not unexpected, because other unoccupied determinants would be available for binding by the commercial polyvalent anti-HBs. These findings therefore suggest that 5D3 IgM anti-HBs is directed toward a highly represented epitope on HBsAg, but also recognizes an epitope shared with the NANB virus.

It should be emphasized that the patients selected for the present Example were part of a much larger group of individuals whose serum gave a positive reaction with the 5D3—5D3 monoclonal assay but not with the commercial RIA. The patient selection was based primarily on very high binding activity of their sera in the monoclonal RIA. Thus, at present it is not clear whether isolates obtained from other sera with lower levels of binding activity will yield the same properties as described above. However, it is evident that the 5D3

IgM material [NANB] may be affinity purified from serum derived from patients with acute and chronic inflammatory liver diseases and even from an normal an individual free of chronic acute hepatitis or acute hepatitis and shows limited crossreactivity with HBsAg when analyzed by conventional anti-HBs reagents. Furthermore this material is not recognized by four other IgM and IgG monoclonal anti-HBs in RIAs, is similar to HBsAg with respect to three polypeptides on NaDodSO4/polyacrylamide gels, has a molecular weight of approximately $2 \times 10^6$, and appears as distinct particles by immunoelectron microscopy.

EXAMPLE 2

Demonstration Of Previously Undetected Hepatitis B Viral Related Determinants In An Australian Aboriginal Population By Monoclonal Anti-HBs Antibody Radioimmunoassays

Subjects

Approximately three-quarters of the adults and children of Mornington Island, an Aboriginal settlement off the mainland of Queensland in the Gulf of Carpentaria were studied The population is very stable and there is little interchange with the mainland. The subjects and the Department of Health, Queensland, gave permission for blood samples to be taken. Peripheral-blood samples were drawn into heparinised tubes, and the plasma was separated by centrifugation.

Production and Characterization of Monoclonal Anti-HBs Antibodies

The immunization protocols, characteristics and purity of the immunization antigen (HBsAg), cell-fusion technique, and growth and cloning of hybridomas producing anti-HBs antibodies have been described previously (Wands et al, Gastroentrology, 80:225-232). The anti-HBs antibodies have been characterized with respect to specificity for determinants on HBsAg, ability to agglutinate red blood cells coated with HBsAg (subtypes adw and ayw), antibody class and subclass, and affinity for HBsAg-associated epitopes. Two IgM and two IgG monoclonal anti-HBs antibodies were selected for this study because they recognize all known subtypes of HBsAg and have very high affinity constants for HBsAg determinants and also recognizes NANB antigenic activity: the monoclonal antibodies 5D3 and 3D4 (IgM), 5C3 (IgG$_{2a}$), and 2C6 (IgG$_1$) have affinity constants of $4 \times 10^{11}$, $8 \times 10^{10}$, $4 \times 10^{10}$, and $2 \times 10^{10}$ litres/moles per molecule, respectively.

Monoclonal IgM and IgG Anti-HBs Radioimmunoassays (Test Procedures)

Previous studies (Shorey, J. et al Hepatology 1:546 (1981) (Abst.)) have established that the 5D3 IgM monoclonal anti-HBs antibody recognizes all known HBsAg subtypes and, more importantly, has the highest affinity constant of the anti-HBs antibodies measured. 5D3 anti-HBs was coupled to a solid-phase support, and the other IgM and IgG antibodies were radiolabelled with iodine-125 to a specific activity of 4–10 $\mu$Ci/$\mu$g . Before iodination the antibodies were purified from ascites fluid by staphylococcal-protein-A affinity chromatography for IgG and 'Sepharose-4B' chromatography for IgM. For the monoclonal radioimmunoassays, approximately 50 ng 5D3-coated beads were incubated with 100 $\mu$l serum and 100 $\mu$l 1 (150,000 cpm) radiolabeled monoclonal anti-HBs for 16 h. The solid-phase support was washed three times with distilled water, and the radioactivity bound to the bead was measured by a Packard gamma well counter.

All serum samples were evaluated with the 5D3—5D3 "simultaneous sandwich" radioimmunoassay in which the antibody on the solid-phase support and the radiolabeled indicator antibody are the same. This assay design is the most sensitive for detection of an HBsAg-related determinant. Once high binding activity was demonstrated in serum, three other monoclonal radioimmunoassays were performed in which radiolabeled 3D4, 2C6, or 5C3 anti-HBs was the indicator probe. It was possible, therefore, to determine whether there were additional antigenic determinants in the 5D3-immunoreactive material which could be detected by the other high-affinity monoclonal antibodies. All serum samples from the Aboriginal population were also tested for HBsAg, anti-HBs, and hepatitis B core antibody (anti-HBc) by commercial radioimmunoassays ('Ausria II', 'Ausab', and 'Corab', respectively; Abbott Laboratories, North Chicago, Ill.).

Analysis of HBs-Ag-related Determinants

Competitive-inhibition studies were carried out to determine whether the four monoclonal anti-HBs antibodies recognize the same, closely related, or separate antigenic determinants on HBsAg. For these investigations HBsAg (subtypes adw and ayw) was coated to a solid-phase support and was incubated for 16 h with a constant concentration of radiolabeled 5D3 (150,000 cpm) and various amounts of purified unlabeled 5D3, 3D4, 2C6, or 5C3 anti-HBs. It would be expected that high concentrations of unlabeled 5D3 would completely inhibit binding of radiolabeled 5D3 to its determinant on HBsAg. If, when another monoclonal anti-HBs such as 2C6 is incubated with radiolabeled 5D3, there is no inhibition of 5D3 binding to HBsAg, it may be concluded that 5D3 and 2C6 bind to different determinants. To provide further evidence in support of this conclusion reverse experiments were performed in which, for example, 2C6 was radiolabeled and incubated with various concentrations of unlabeled 5D3. If there is no inhibition of binding of the labeled antibody in the presence of a high concentration of the other, unlabeled antibody, the two antibodies must be directed against distinct and separate determinants on the hepatitis-B-virus related protein.

Results

Figure 4:
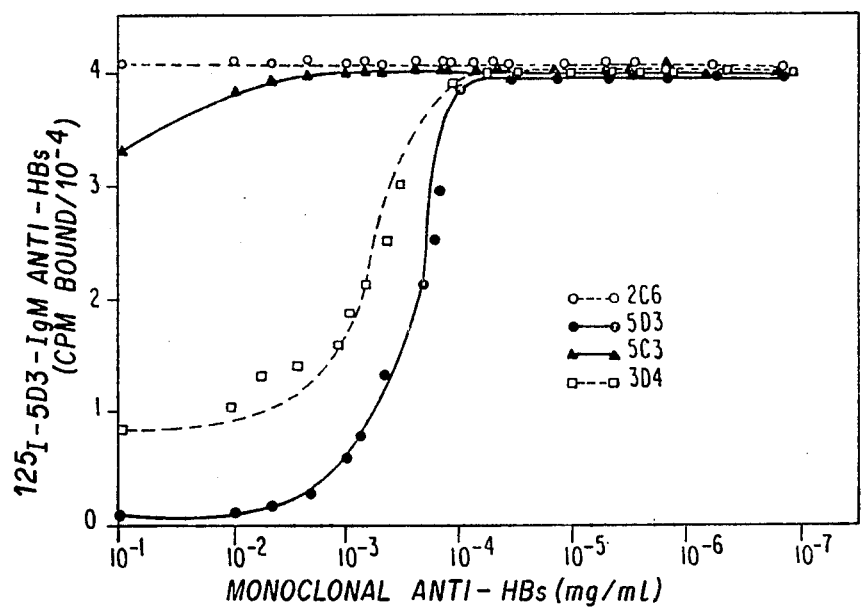
FIG. 4 shows the comparative inhibition of binding to HBsAg determinants by monoclonal anti-HBs antibodies (See Example 2). The IgG anti-HBs antibodies 2C6 and 5C3 have no effect on the binding of 5D3 to HBsAg-related determinant(s), whereas 3D4, an IgM anti-HBs, partially inhibited 5D3 binding.

The IgG anti-HBs antibodies 2C6 and 5C3 had no effect on the binding of 5D3 to an HBsAg-related determinant (FIG. 4), whereas 3D4, an IgM anti-HBs, partially inhibited 5D3 binding. Additional experiments confirmed that 5C3, 2C6, and 5D3 recognized distinct and separate determinants on HBsAg. There was some antigenic cross-reactivity between the 5D3 and 3D4 epitopes; 3D4 binding was not, however, influenced by the two IgG antiHBs HBs antibodies (5C3 and 2C6). The four monoclonal radioimmunoassays used in this study detect three separate epitopes and one partially cross-reactive epitope on HBsAg.

Approximately 50% of the study population had been exposed to HBV as shown by the presence in serum of HBsAg, anti-HBs and anti-HBc, or both antigen and antibodies (Table 2).

TABLE 2

HEPATITIS B VIRUS MARKERS IN MORNINGTON ISLAND RESIDENCE

| Patient group* | No. with marker (%) | | | Positive by | |
|---|---|---|---|---|---|
| | Anti—HBs | AntiHBc | Anti—HBs anti+HBc | Ausria II | 5D3 RIA |
| Adult men (n = 96) | 23(24.9) | 7(7.3) | 27(28.1) | 5(5.2) | 7(7.3) |
| Adult women (n = 73) | 13(17.8) | 7(9.6) | 15(20.5) | 5(6.8) | 10(13.7) |
| Male children (n = 57) | 5(8.7) | 1(1.7) | 15(26.3) | 2(3.5) | 5(8.8) |
| Female children (n = 50) | 4(8.0) | 1(2.0) | 6(12.0) | 1(2.0) | 6(12.0) |
| Total+ (n = 316) | 51(16.1) | 22(6.98) | 73(23.0) | 14(4.4) | 31(9.8) |

*Analysis on 276/316 subjects for whom data on age and sex were available.
+Total population was 316 subjects.

14 subjects were positive for HBsAg by the commercial radioimmunoassay (AUSRIA II); all were highly positive by the 5D3—5D3 simultaneous sandwich monoclonal radioimmunoassay, as were 17 other subjects who were negative by commercial RIA (AUSRIA II). There was a higher frequency of hepatitis B VIRUS markers in male subjects of all ages than in female subjects.

TABLE 3

DEMONSTRATION OF HBV-RELATED VIRAL DETERMINANTS BY MONOCLONAL-ANTIBODY BINDING

| Sample No. | Anti—HBs | Anti—HBc | S/N* measured by | | | | |
|---|---|---|---|---|---|---|---|
| | | | Ausria II | 5D3-5D3 | 5D3-5C3 | 5D3-2C6 | 5D3-3D4 |
| 1 | — | — | 0.6 | 8.3 | 4.1 | 0.7 | 6.4 |
| 2 | — | — | 0.4 | 11.0 | 1.0 | 0.5 | 4.3 |
| 3 | + | + | 0.7 | 4.1 | 0.5 | 4.1 | 0.6 |
| 4 | — | — | 1.1 | 4.1 | 8.0 | 1.2 | 6.4 |
| 5 | + | +. | 0.3 | 13.0 | 0.6 | 0.3 | 17.0 |
| 6 | + | — | 0.1 | 4.0 | 8.0 | 0.5 | 1.3 |
| 7 | — | — | 0.9 | 23.0 | 2.1 | 1.1 | 3.5 |
| 8 | + | + | 1.3 | 7.1 | 0.6 | 0.7 | 2.8 |
| 9 | — | + | 0.7 | 5.4 | 5.4 | 0.7 | 2.0 |
| 10 | — | — | 0.9 | 9.7 | 0.3 | 0.9 | 6.3 |
| 11 | + | — | 0.8 | 3.1 | 0.6 | 0.5 | 2.1 |
| 12 | — | — | 1.1 | 11.0 | 0.9 | 0.9 | 1.9 |
| 13 | + | + | 1.3 | 15.0 | 0.6 | 0.6 | 2.4 |
| 14 | — | — | 0.4 | 3.9 | 0.3 | 0.3 | 1.6 |
| 15 | + | — | 0.4 | 11.0 | 1.4 | 0.4 | 4.1 |
| 16 | — | + | 0.8 | 5.5 | 0.4 | 0.5 | 2.0 |
| 17 | + | + | 1.7 | 7.0 | 0.8 | 0.4 | 1.7 |
| Total (n = 17) | 8(47%) | 7(41%) | 0(0%) | 17(100%) | 5(29%) | 1(6%) | 12(71%) |
| Controls + AA (n = 14) | 0(0%) | 14(100%) | 14(100%) | 14(100%) | 14(100%) | 14(100%) | 14(100%) |
| BD (n = 100) | 7(7%) | 5(5%) | 0 | 1(1%) | 1(1%) | 0 | 2(2%) |

*S/N represents signal/noise calculated as mean cmp bound in experimental samples divided by the mean cpm of the negative controls. Result considered positive if S/N ≧ 2 · 0.
No. (%) of subjects positive.
Australian Aborigines' samples positive by AUSRIA II radioimmunoassay. All samples were reactive with monoclonal anti—HBs IgM and IgG antibodies.
BD = blood donors.

In addition to the 14 HBsAg-positive subjects shown in Table 2, the 5D3—5D3 monoclonal radioimmunoassay demonstrated significant binding activity in 17 other subjects. The results of further monoclonal-antibody analysis of these samples are given in Table 3. Several patterns were observed. For example, positive results were obtained in sample 1 by the 5D3—5D3, 5D3—3D4, and 5D3—5C3 radioimmunoassays but not by the commercial radioimmunoassay (AUSRIA II) or by the 5D3—2C6 radioimmunoassay. Samples from other subjects, such 2, 5, and 8 were HBsAg-positive by only the 5D3—5D3 and 5D3—3D4 assays; in each of these cases 5D3 was coupled to the solid-phase support and the other $^{125}$I-labelled monoclonal IgM and IgG anti-HBs served as the indicator probe. It is likely that the 5D3-reactive material and bound to the solid-phase support but was not detected by some of the radioimmunoassays with other monoclonal anti-HBs antibodies because the HBsAg viral determinants they recognise were absent or not available in sufficient concentration. It is not surprising that there was binding activity with 3D4 antibody in 12 of 17 (71%) 5D3-positive samples, since competitive-inhibition studies indicated partial antigenic cross-reactivity between the 5D3 and 3D4 determinants. The positivity rate for all the monclonal radioimmunoassays was negligible in a low-incidence blood-donor population (Table 3); this finding provides further evidence of the specificity of the monoclonal radioimmunoassays for HBsAg-related determinants.

Discussion

It has been found that more than 50% of the Aboriginal community on Mornington Island had been exposed to HBV. A very high rate of infection with HBV would be expected in confined Aboriginal communities such as that on Mornington Island because of the amount of close contact within household group, the poor socio-economic conditions, and the very high incidence of venereal disease.

The specificity of the high-affinity IgM and IgG monoclonal antibodies has been confirmed by this Example. The antibodies were prepared against HBsAg, and each has been demonstrated to react specifically with known HBsAg subtypes. Competitive-inhibition experiments indicate that the antibodies recognise distinct and separate determinants on HBsAg. All serum samples which reacted with conventional polyvalent anti-HBs antisera (AUSRIA II) also reacted strongly with the four monoclonal anti-HBs IgG and IgM antibodies, and serum samples from a control caucasian population known to have a low incidence of HBV exposure, reacted infrequently with the monoclonal antibodies. The dilution curves for antibody binding to HBsAg in serum are remarkably similar, which indicated that these viral determinants are present in high frequency on HBsAg and that they are distributed homogenously in the population.

The 17 subjects whose serum was reactive in the 5D3—5D3 monoclonal radioimmunoassay but was negative when tested by polyvalent conventional anti-HBs anti-sera are particularly relevant to this invention. The 5D3—5D3 radioimmunoassay has a sensitivity of 100 pg/ml serum for an HBsAg-related determinant, which represents a sensitivity several times greater than that of the commercial radioimmunoassay. Therefore, some of the positive results may be explained on the basis of the greater sensitivity of the assay but other positive results cannot be explained by this mechanism. Other monoclonal radioimmunoassays using antibodies which recognize different HBsAg determinants have demonstrated enhanced binding activity in substantial numbers of the 5D3-positive samples. These findings add further support to the concept that the 5D3 binding activity is related to the presence of the NANB hepatitis-B-related viral determinants in serum. In Example 1 were investigated serum samples that exhibited high binding activity in the 5D3—5D3 monoclonal radioimmunoassay but were negative by AUSRIA II, and some of the properties of the binding material were characterized, supra. The finding of antigenic determinants recognized only by high-affinity monoclonal antibodies in a high proportion of the Mornington Island population without conventional HBV markers, indicates that there are additional viruses in this community antigenically related to HBV but not previously detected, i.e., NANB virus. This will be proved by subsequent example (See below).

EXAMPLE 3

Demonstration of NANB viral DNA in Human Serum

Materials and Methods

Serum Specimens and RIA's—Serum Specimens and RIA's were those of Examples 1 and 2.

Because several individuals who were reactive only in monoclonal RIAs had anti-HBs and anti-HBe antibodies in the serum, additional experiments were performed to ascertain sentitivity of the monoclonal RIA for an HBsAg-related determinant in the HBsAg-anti-HBs immune complexes formed at various antigen/antibody ratios. In these investigations, several chronic carriers of HBsAg were selected, and serial dilutions were made of their serum (with HBsAg-negative serum). Binding activity was measured in each specimen by monoclonal RIAs and was compared to that obtained with polyvalent anti-HBs antibodies (AUSRIA II).) Dilution of HBsAg-positive serum (200 μl) was then incubated with 25 μl of serum from a multiply transfused hemophiliac patient (with an anti-HBs titer of $1-2.2 \times 10^6$ by passive hemaaggultination) for 12 hr at 20° C. After this incubation, the RIAs were performed; monoclonal anti-HBs and AUSRIA II for HBsAg and AUSAB for anti-HBs levels.

HBV DNA Hybridization Studies—For molecular hybridization studies, 10 μl aliquots of human serum were applied to nitrocellulose filter sheets and denatured and fixed to the filter with 0.5M NaOH. The material was neutralized, on the filter, with 0.5M Tris-HCL pH 7.4–1.5M NaCl, digested with proteinase K (200 μg/ml in 0.3M NaCl/0.03M Na citrate, air dried, and baked in vacuo at 80° C. for 2 hr. The bound DNA was prehybridized and hybridized with HBV [$^{32}$P] DNA. For these experiments, recombinant cloned HBV DNA ($\approx$3,250 base pairs) was repurified from plasmid pAOl HBV DNA by digestion of the plasmid with restriction endonuclease EcoRI, followed by agarose gel electrophoresis and electroelution of the purified HBV DBA band. HBV DNA was labeled with [$^{32}$P]dCTP and [$^{32}$P]dATP to a specific activity of $2-4 \times 10^8$ cpm/μg of DNA by nick-translation. Hybridization was performed in 0.75M NaCl/0.075M Na citrate/0.02% polyvinylpyrrolidone/0.02% Ficoll/0.02% bovine serum albumin containing denatured calf thymus DNA (150–200 μg/ml) and heat-denatured HBV[$^{32}$p]DNA ($1 \times 10^6$ cpm/ml) at 65° for 24–36 hr. After hybridization, the unreacted solution was discarded, and the nitrocellulose filter was washed, dried, and autoradiographed. For control experiments, the test sample was purified HBV DNA, DNA extracted from the PLC/PRF/5 cell line, which contains 5 or 6 copies of HBV DNA per genome equivalent or DNA isolated from serum Dane particles.

Results

Figure 5:
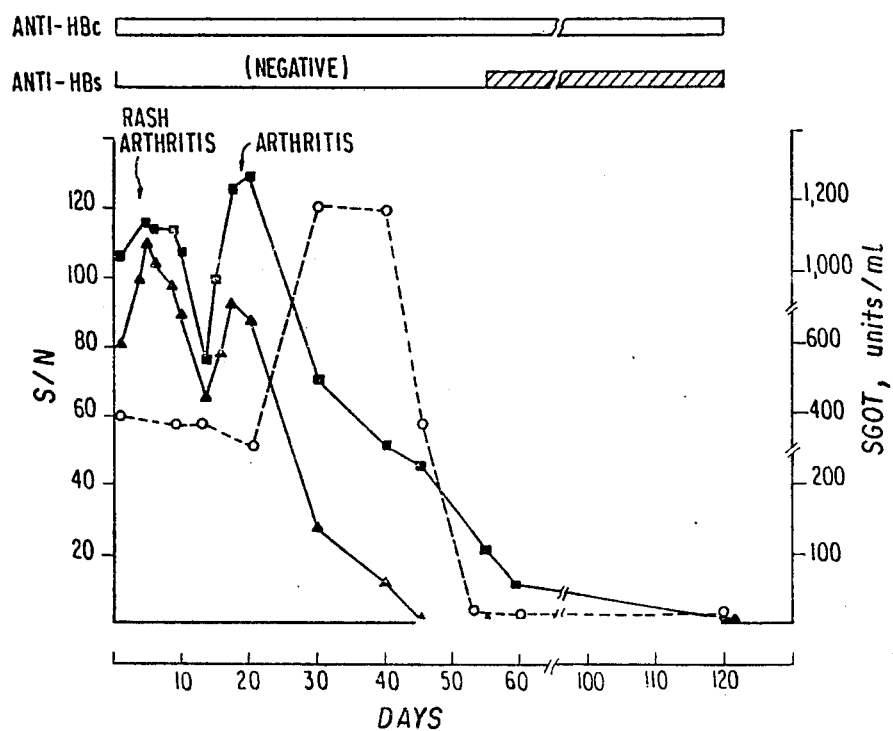
FIG. 5 shows a comparison of the IgM monoclonal RIA (■) with polyclonal antibody AUSRIA II (▲) patient with acute hepatitis B and immune complex disease. ---O---SGOT (serum alanine amino transferase). S/N, signal-to-noise ratio defined as CPM bound in experimental samples/CPM bound in controls (See Example 3)

FIG. 5 depicts a serial study on a patient with acute hepatitis B and HBsAg-anti-HBs immune complex disease characterized by arthritis, rash and arthralgias. In thss figure, the signal/noise ratio for HBsAg (a measure of specific binding activity) is higher with monoclonal anti-HBs (IgM) than with polyvalent antiHBs (AUSRIA II). More importantly, the monoclonal RIA for HBsAg remained positive for $\approx$3 wk after the polyvalent AUSRIA II RIA had become negative. During this period, anti-HBs was present in the serum, suggesting that the monoclonal RIA may detect HBsAg-related detemiant in HBsAg-anti-HBs immune complexes formed in anti-HBs excess and that such determinants are not detectable by polyvalent anti-HBs antisera.

To further explore this possibility, two additional studies were performed in which HBsAg-anti-HBs immune complexes were formed in vitro with serum from a chronic HBsAg carrier by the addition of high titer polyvalent anti HBs antibodies. When polyvalent anti-HBs was added to serum from an HBsAg carrier, the sequences, 36 selected specimens previously characterized by monoclonal RIAs and additional samples were hybridized under code with HBV[$^{32}$P]DNA (Table 4).

TABLE 4

Characteristics of patients whose serum was reactive by both monoclonal RIAs and HBV DNA Hydridization

| No. | Diagnosis | AUSRIA II RIA, cpm bound | Monoclonal RIA, cpm bound | Anti —HBs | Anti —HBc | HBV-DNA Related Sequences |
|---|---|---|---|---|---|---|
| 1 | Acute hepatitis | 93 | 2,641 | + | — | + |
| 2 | Chronic active hepatitis | 141 | 7,621 | — | — | + |
| 3 | Post-transfusion hepatitis* | 136 | 2,193 | — | — | + |
| 4 | Blood donor | 147 | 1,862 | — | — | + |
| 5 | Blood donor | 141 | 2,613 | — | — | + |
| 6 | Blood donor | 96 | 1,562 | — | — | + |
| 7 | Blood donor | 114 | 684 | — | — | + |
| 8 | Aus. abor. | 119 | 1,281 | — | — | + |
| 9 | Aus. abor. | 88 | 691 | + | + | + |
| 10 | Aus. abor. | 94 | 663 | + | + | + |
| 11 | Aus. abor. | 110 | 934 | + | — | + |
| 12 | Aus. abor. | 113 | 2,600 | + | + | + |
| 13 | Aus. abor. | 138 | 1,084 | + | + | + |
|  | Controls (100) | 136 ± 17 | 56 ± 9 |  |  |  |

Aus. abor., Australian aborigine.
*Recipient of blood from patient 4.
Incriminated in transmitting post-transfusion hepatitis. Serum was not available for analysis for recipient of blood from patient 6.

monoclonal RIA (anti-HBs IgM) remained positive up to a 10-fold greater dilution than did the AUSRIA II RIA. When, in place of IgM monoclonal anti-HBs, studies were carried out with IgG monoclonal anti-HBs 5C3 and 5C11, which recognize distinct and separate determinants on HBsAg, similar results were obtained. These findings indicate that monoclonal anti-HBs RIAs can recognize specific viral epitopes in the immune complexes when HBsAg is no longer detectable by polyvalent anti-HBs antibodies.

To determine whether HBV DNA-related sequences were present in serum samples that were positive for HBsAg by RIAs only with monoclonal anti-HBs antibodies, sera (10 μl aliquots) were applied as spots to a nitrocellulose filter sheet and denatured. The DNA material was fixed, hybridized with recombinant-cloned and repurified HBV [$^{32}$P]DNA, washed, and autoradiographed. All experiments were preformed under code with two investigators independently interpreting the autoradiograms. A series of control samples either positive or negative for HBsAg by AUSRIA II were correspondingly positive or negative for HBV DNA by hydridization, respectively. In several hundred random or unselected specimens from a clinical laboratory analyzed, there was no instance in which the HBV DNA hydridization test was positive when the AUSRIA II RIA was negative.

In a select group of specimens that were positive for HBsAg by RIA with $^{125}$I-labeled monoclonal anti-HBs IgM (5D3) but were negative by RIA with $^{125}$I-labeled polyvalent anti-HBs(AUSRIA II), HBV[$^{32}$P]DNA hydridization was performed. Three of seven samples were positive for HBV DNA by molecular hybridization. Unlike random specimens from a clinical laboratory, some of these specimens which contain HBsAg-related antigenic activity as detected by 5D3 anti-HBs RIA (i.e., NANB virus protein) also contained HBV-DNA-related sequences (i.e., NANB virus DNA) as detected by molecular hybridization with purified HBV-DNA.

To determine the frequency with which sera negative for HBsAg by AUSRIA II but positive for monoclonal anti-HBsAg were positive also for HBV-related DNA sequences, 36 selected specimens previously characterized by monoclonal RIAs and additional samples were hybridized under code with HBV[$^{32}$P]DNA (Table 4).

Table 4 lists the results together with clinical information and data from other tests including various RIAs. A total of 13 of 36 samples (36%) of specimens from different individuals positive for HBsAg determinants with monoclonal anti-HBs but negative with polyvalent anti-HBs were positive for HBV DNA sequences by hybridization with recombinant-cloned and repurified HBV DNA. Amongst these individual were three patients with acute or chronic hepatitis, four blood donors (two of whom have been implicated in transmission of hepatitis to recipients of their blood), and six Australian aborigines of the isolated population from Mornington Island where HBV infection is endemic (See Example 3).

Discussion

In the present Example, the monoclonal RIA is able to bind to viral epitopes in HBsAg-anti-HBs immune complexes formed in the presence of anti-HBs excess. Possible explanations for this phenomenon are: (i) the high-affinity monoclonal anti-HBs may compete more effectively for their determinant(s) than do naturally occurring anti-HBs or (ii) the antibodies may have access to unoccupied determinants in the presence of polyvalent anti-HBs excess. Thus, polyvalent anti-HBs may contain only a small amount of antibody with immunologic properties of 5D3, 5C3 and 5C11 monoclonal antibodies, and, even though immunogenicity is directed against HBsAg-related determinants, the region of immunologic reactivity with the monoclonal antibodies may extend beyond that present in polyvalent antisera. Such a phenomenon could permit detection of HBAg in immune complexes by monoclonal RIAs, whereas conventional anti-HBs antibodies would demonstrate no binding activity under conditions of anti-HBs excess.

Although such activity could explain the detection of HBsAg in the presence of excess anti-HBs (Table 4 cases 1 and 9-13) additional consideration is required concerning the positive binding activity observed in patients negative for HBsAg by AUSRIA II RIA who where also anti-HBs negative (Table 4 cases 2-8). Some of these results may be explained by the increased sensitivity of the monoclonal immunoassays for HBsAg-associated determinants as demonstrated by the present and previous examples. In addition, HBsAg in some patients may be present in immune complexes circulating under conditions of anti-HBs equivalence or excess and, as shown here, would be detectable only by monoclonal RIAs.

In terms of the HBV DNA reacting sequences present in 36% of serum specimens positive for HBsAg by monoclonal RIAs but negative by polyvalent RIAs-(AUSRIA II) the results indicate that DNA sequences related to or homologous with HBV DNA are present in these specimens. Aside from these selected cases, hybridization with human serum negative for HBsAg by the AUSRIA II RIA has not been detected thus far. Therefore, the present findings do not represent biologically false-positive results.

The presence of both immunoreactive material and hybridizable DNA sequences provides corroborative evidence for the the presence of the NANB virus in a significant proportion of these specimens. Positive results were found for both tests under circumstances in which no HBV markers in serum were detected by commercially available RIA (cases 2-7, Table 4). It should be noted that integrated HBV-DNA has been reported in human hepatocellular carcinoma tissue under circumstances in which serum of said patients was negative for HBsAg, anti-HBs and anti-HBc by commercial Abbott kits (Brechot, C. et al, Hepatology, 1, 499 (abstract 9B), 1981 and Brechot, C. et al Hepatology 2, supplement, 27S—34S, 1982 and herein incorporated by reference).

EXAMPLE 4

Infectivity Studies Of Viral Hepatitis In Chimpanzees: Characterization Of NANB Hepatitis B Virus Agents RIA's, HBV-DNA hybridization and antibody specificity were as described in Examples 1-3, supra.

Infectivity Studies

Two chimpanzees were inoculated with one mililiter of serum derived from an individual ho had been incriminated in transmitting "non-A, non-B" hepatitis through blood transfusions. Another chimpanazee was injected with 40 mililiters of a clotting factor concentrate previously shown to transmit "non-A, non-B" hepatitis to recipients. The final chimpanzee was inoculated with one mililiter from another individual suspected to harbor a "non-A, non-B" hepatitis agent. Serial studies were performed and immunoreactivity in serum was measured serially by four monoclonal anti-HBs, RIAs, the presence of HBV-related DNA sequences by molecular hybridization analysis, HBsAg by AUSRIA II RIA, antibodies to hepatitis B core antigen (anti-HBc) and anti-HBs (CORAB and AUSAB respectively; Abbott Laboratories, North Chicago, Ill.) and on selected samples, IgM antibody to hepatitis A virus (HAVAB; Abbott Laboratories).

Results

Figure 6:
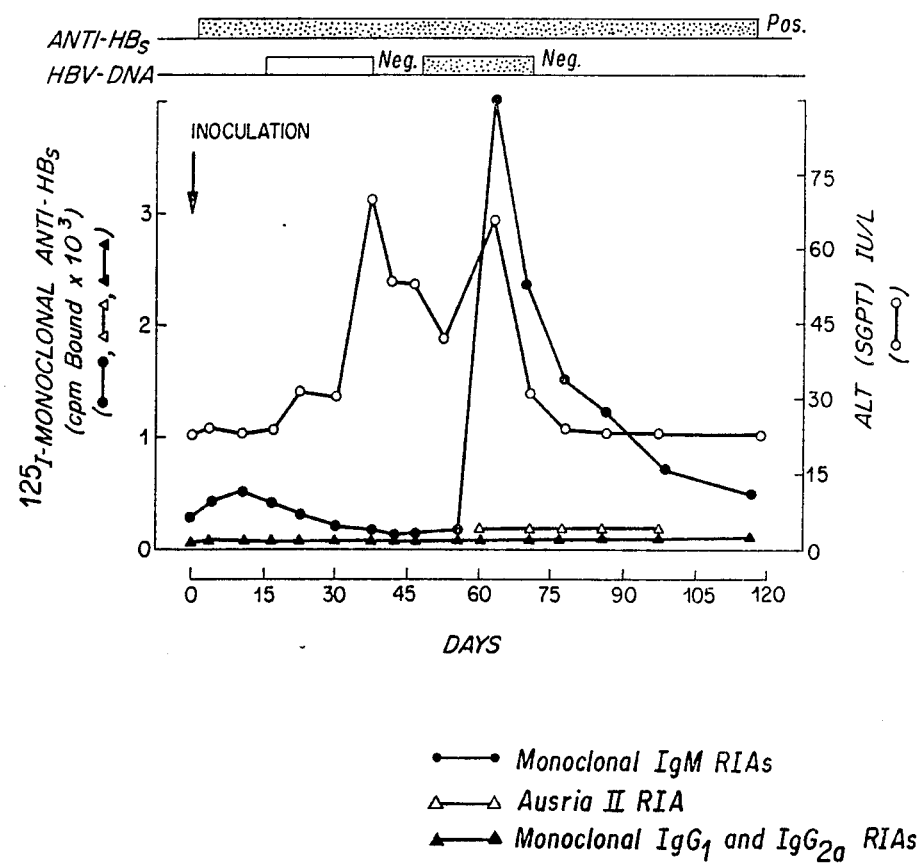
FIG. 6 shows the clinical and virologic course of non-A, non-B hepatitis in a chimpanzee. The elevations of ALT precede the appearance of antigen and HBV-related DNA sequences in the blood (See Example 4, for this and for FIGS. 7–10)
Figure 7:
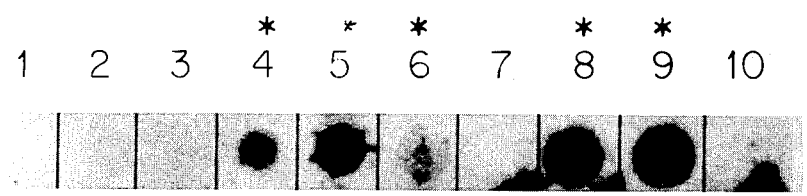
FIG. 7 shows the detection of hepatitis B-virus-DNA related sequences by molecular hybridization analysis in 250 μL serum from two chimpanzees with non-A, non-B hepatitis. *: Denotes positive results with a recombinant, cloned HBV-DNA probe. Spots 1, 2 and 3 were negative for HBV-DNA but positive for antigen by IgM anti-HBs radioimmunoassays (see FIGS. 9 and 10). Spots 4, 5 and 6 were positive for both antigen and HBV-DNA related sequences in serum on days 47, 58 and 64 (FIG. 6). Spots 8 and 9 were also positive for antigen and HBV-related sequences on days 190 and 204 in the second animal (FIGS. 8). Spots 7 and 10 are negative controls.

FIG. 6 depicts the observations in a chimpanzee inoculated with the clotting factor concentrate. This animal had previously recovered from HBV infection and was positive for anti-HBs at the time of inoculation and throughout the study period. This chimpanzee was therefor immune to HBV infection as currently recognized and defined. The first evidence of liver injury was apparent on day 40 with a rise in ALT levels to 70 IU/L (ml <38 IU/L); ALT elevations persisted for approximately 35 days. Immunoreactive antigen appeared briefly in low titer following inoculation of 40 mililiters of clotting factor concentrate and then disappeared from the circulation. On day 64 there was a striking rise in serum IgM anti-HBs binding activity from a baseline of 50 CPM to 4010 CPM (S/N≃80, nl <2.1). Antigenemia was subsequently present in the blood for 56 days although titers fell with resolution of the hepatitis. It is noteworthy that ALT levels reached normal values by day 78 but antigen was still detectable in the blood for an additional 42 days. Most importantly, the rise in ALT levels preceded the development of antigenemia and/or viremia by approximately 30 days and thus gives a more accurate description of the incubation period of 64 days (e.g., 24 days after the first ALT rise). Correlations were then made between the appearance of antigen in the blood and the presence of HBV-related DNA hybridizable sequences. As a control, HBV related nucleic acid sequences were not detected during the incubation period by molecular hybridization analysis. In contrast, there was a striking correlation between the rise in antigen titers and the presence of nucleic acid material which hybridized to the HBV-DNA probe suggesting that virions were released into the circulation, FIG. 7. With respect to other HBV related epitopes, the 5C3 or 5C11 determinants were not detected in serum by RIAs. This observation indicates that NANB virus is antigenically distinct from HBV. Finally, a RIA which employs polyvalent anti-HBs antibodies (AUSRIA II) was unreactive during the course of infection and anti-HBc and anti-HA antibodies were undetectable.

Figure 8:
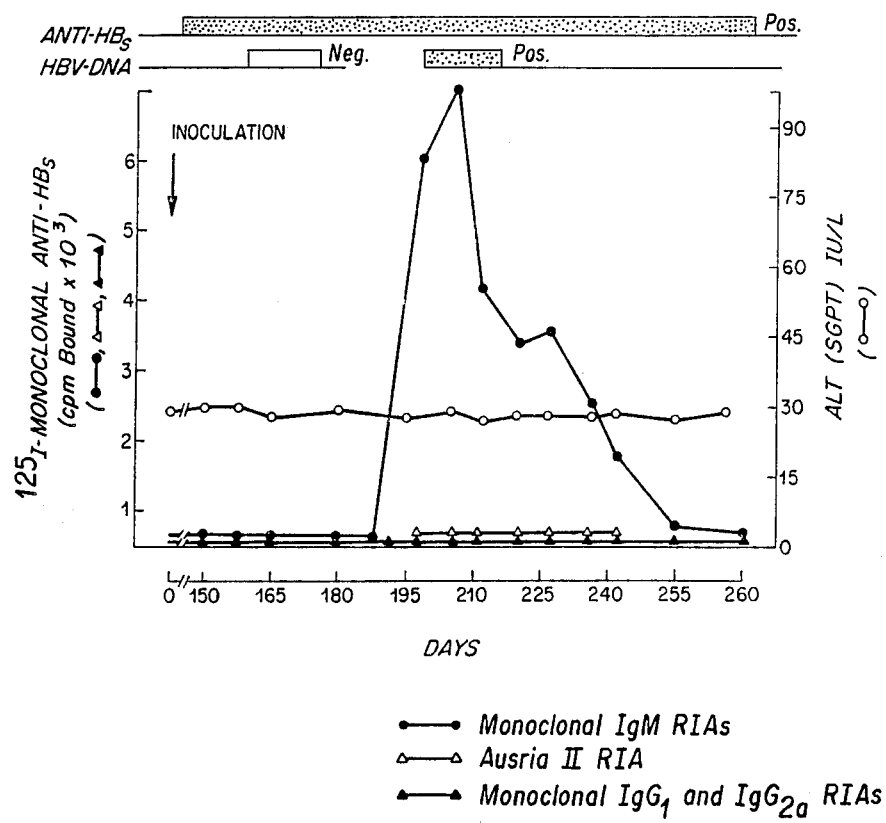
FIG. 8 shows the clinical and virologic course of non A, non B hepatitis in a chimpanzee. Despite infection, as shown by the presence of viral antigen and HBV-DNA related sequences in serum, ALT values remained normal.

FIG. 8 demonstrates the clinical and virologic course of a second chimpanzee with pre-existing anti-HB inoculated with 1 mililiter of serum carrying a "non-A, non-B" agent. In contrast to FIG. 6, there was no rise in ALT levels during the observation period. The incubation time was judged to be approximately 190 days. The level of antigenemia as reflected by the peak binding activity of the IgM monoclonal RIA was, however, impressive indeed (S/N≃175). The period of antigenemia was prolonged (approximately 65 days), and antigen levels became undetectable by day 260. Similar to the first chimpanzee as shown in FIG. 6, HBV-related DNA sequences were undetectable during the incubation period but were present by HBV-DNA hybridization at the peak of monoclonal IgM RIA binding activity. Moreover, other HBV related epitopes were absent as determined by the monoclonal RIAs as well as HBsAg (AUSRIA II), anti-HBc and anti-HA antibodies.

Figure 9:
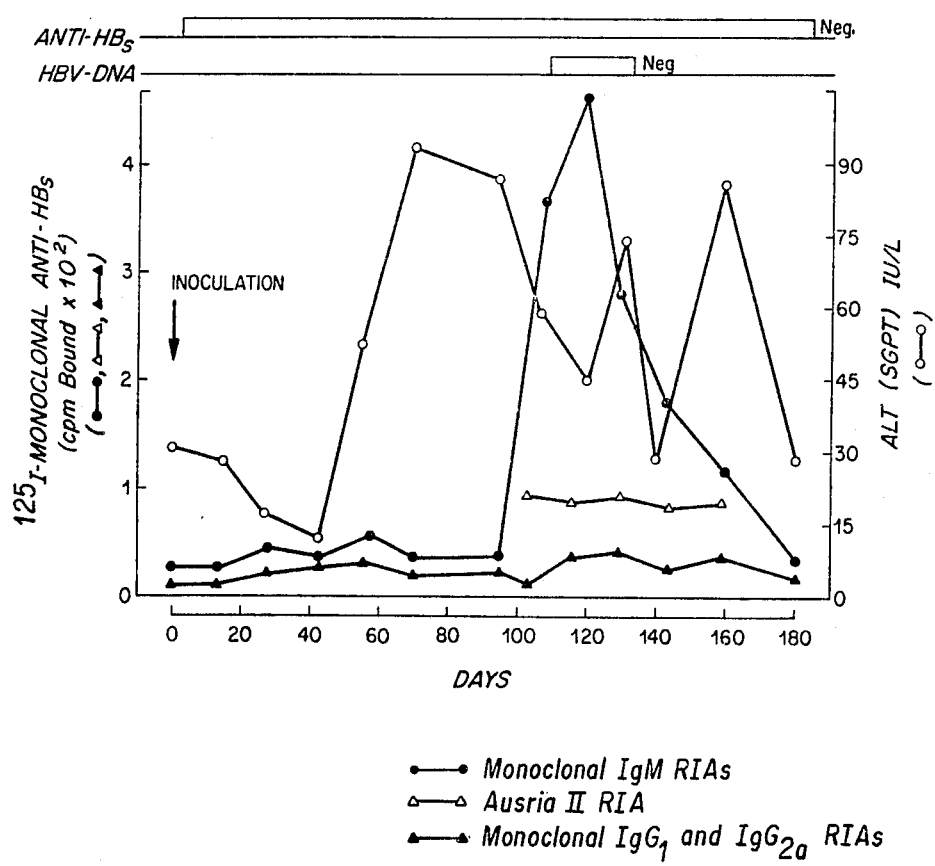
FIG. 9 shows the clinical and virologic course of non A, non B hepatitis in a chimpanzee. Similar to FIG. 6, ALT elevations precede the appearance of antigen detected by the monoclonal IgM anti-HBs radioimmunoassays by approximately 45 days. HBV-DNA related sequences were not detected in this animal.
Figure 10:
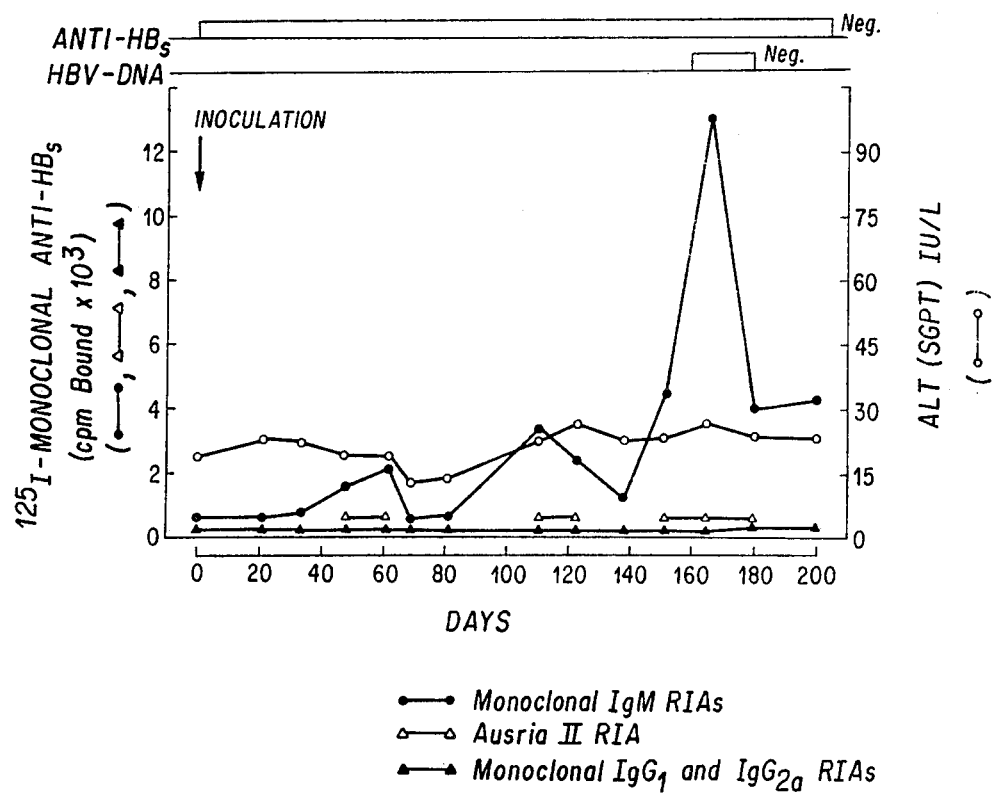
FIG. 10 shows the clinical and virologic course of non A, non B hepatitis in a chimpanzee. The appearance of three well defined peaks of antigenemia as measured by the monoclonal IgM anti-HBs radioimmunoassays should be noted.

FIGS. 9 and 10 illustrate the clinical and virologic course of the final two chimpanzees inoculated with 1 mililiter (each) of serum derived from another individual who had been incriminated in transmitting "non-A, non-B" hepatitis. In FIG. 9, evidence of liver injury as demonstrated by ALT elevations was apparent on day 50 and persisted with a relapsing pattern for 140 days. Antigenemia appeared on day 92. Antigen titers were, however, falling by day 130 and reached undetectable levels on day 180. The magnitude of peak binding activity by monoclonal RIA was less (S/N≃10) than that observed in previous studies. It should be noted that anti-HBs was not present at the time of inoculation or during hepatitis infection and recovery. Similar to the chimpanzee shown in FIG. 6, the rise in ALT levels precedes the appearance of antigen in the blood by approximately 50 days. HBV-related DNA hydridizable sequences were not detectable nor were other HBV associated epitopes, HBsAg, anti-HBc and anti-HA antibodies.

FIG. 10 represents the second chimpanzee inoculated with the same serum. In contrast to the pattern seen in FIG. 9, ALT elevations were absent. This was similar to the pattern observed in FIG. 8. There were three well defined spikes of antigenemia with the highest values occuring on day 164. HBV-related DNA sequences were not detectable during any of the episodes of antigenemia. This chimpanzee was also negative for HBsAg, other HBV related epitopes, anti-HBc, anti-HBs (before, during and after infection) and anti-HA antibodies.

In the present Example it is shown that the agent(s) identified by the techniques of Examples 1-3 is (are) infectious by infectivity studies of viral hepatitis in chimpanzees.

Thus, it has been possible to reproduce the findings in man (See Example 3, Table 4) in an accepted experimental animal model of "non-A, non-B" hepatitis. The major observations in the present Example include: (1) three different inocula injected into 4 animals were infectious; (2) the incubation period, defined as the time from inoculation of infections material to the appearance of virus or viral protein in the blood is longer than previously recognized; (3) ALT elevations may precede the appearance of antigenemia by several weeks; (4) antigenemia may occur in the absence of ALT elevations; a phenomenon identical to that observed in man; (5) the presence of antigen in the blood as measured by the monoclonal IgM anti-HB RIAs correlates well with the appearance of HBV-related DNA like sequences by molecular hybridization analysis; (6) the period of antigenemia and/or viremia may persist for weeks to months and usually disappears with recovery; (7) antigenemia is still detectable in the resolution phase of illness when ALT levels are normal, which is similar to HBV infection in man; (8) several episodes of antigenemia may occur during the course of infection; (9) pre-existing anti-HBs was not protective and thus NANB virus is sufficiently different in antigenic composition than HBV. In support of this concept is the finding that polyvalent anti-HBs antibodies (AUSRIA II) and other monoclonal anti-HBs which recognize different HBsAg associated epitopes were unreactive. Taken together these and the previous examples provide strong evidence that NANB hepatitis agents in many circumstances may be a related but distant or distinct variant of hepatitis B virus.

Having now fully described this invention it will be apparent to those of skill in the art that the same can be performed within a wide and equivalent range of methods, tests, compositions, procedures and processes without affecting the spirit or scope of the invention or of any embodiment thereof.

What is new and intended to be covered by Letters Patent of the United States is:

1. A method of diagnosing the NANB disease state in an animal sample which comprises the steps of:
   (A) confirming the presence of a disease state which is either HBV or NANB in said sample by means of an immunoassay which utilizes a monoclonal antibody which is cross-reactive with HBV viral protein and which is not specific for HBV viral protein; and
   (B) positively identifying the presence of the NANB disease state by confirming the absence of HBV viral protein by means of an immunoassay utilizing a monoclonal antibody which is HBV specific.

2. The method of claim 1 wherein said step A immunoassay is performed using a monoclonal IgM antibody or viral protein.

3. The method of claim 2 wherein said immunoassay method is a sandwich immunoassay.

4. The method of claim 3 wherein said sandwich immonoassay utilizes a first solid phase bound IgM monoclonal antibody and a second detectably labeled IgM monoclonal antibody.

5. The method of claim 1 wherein said monoclonal antibody of step B is an IgM antibody obtained from cell line ATCC CRL 8018.

6. The method of claim 1 wherein said monoclonal antibody of step B is an IgG antibody obtained from cell line ATCC HB 8171.

7. The method of claim 1 wherein said step (a) comprises a sandwich immunoassay using a first solid phase bound IgM monoclonal antibody obtained from cell line ATCC HB 9801 and a second detectably labeled IgM monoclonal antibody obtained from cell line ATCC HB 9801; and said step (B) comprises an immunoasay utilizing a monoclonal antibody obtained from a cell line selected from the group consisting of ATCC CRL 8018 and ATCC HB 8171.

8. The method of claim 1 wherein said sample is serum or blood obtained from an animal.

9. The method of claim 8 wherein said animal is a human.

10. The method of claim 9 wherein said sample is human blood to be transfused.

11. The method of claim 2 wherein said IgM antibody is derived from a cell line selected from the group consisting of ATCC HB 9801 or ATCC HB-8170.

12. The method of claim 1 wherein said IgM antibody is derived from cell line ATCC HB 9801.

13. The method of claim 4 wherein both said monoclonal antibodies are obtained from cell line ATCC HB 9801.

* * * * *